United States Patent [19]

Renz et al.

[11] Patent Number: 5,507,937
[45] Date of Patent: Apr. 16, 1996

[54] PLANAR ELECTROCHEMICAL PROBE

[75] Inventors: Hans-Joerg Renz, Leinfelden-Echterdingen; Harald Neumann, Vaihingen, both of Germany

[73] Assignee: Robert Bosch GmbH, Stuttgart, Germany

[21] Appl. No.: 325,101

[22] Filed: Oct. 18, 1994

[30] Foreign Application Priority Data

Dec. 9, 1993 [JP] Japan ............... 43 42 005.2

[51] Int. Cl.⁶ ............................................. G01N 27/407
[52] U.S. Cl. ...................................... 204/426; 204/425
[58] Field of Search ............................. 204/421–429

[56] References Cited

U.S. PATENT DOCUMENTS

| | | | |
|---|---|---|---|
| 4,797,194 | 1/1989 | Mase et al. | 204/426 |
| 4,859,307 | 8/1989 | Nishizawa et al. | 204/429 |
| 5,098,549 | 3/1992 | Friese et al. | 204/426 |
| 5,145,566 | 9/1992 | Logothetis et al. | 204/426 |
| 5,169,512 | 12/1992 | Wiedenmann et al. | 204/426 |

*Primary Examiner*—T. Tung
*Attorney, Agent, or Firm*—Spencer & Frank

[57] ABSTRACT

A planar electrochemical probe includes a probe body laminated together from a plurality of solid electrolyte layers and having integrated into the probe body a gas measurement chamber which is connected to the measurement gas via a diffusion hole. The diffusion hole has a depth that extends beyond the gas measurement chamber into a solid electrolyte layer adjoining the gas measurement chamber. The manufacture of the planar electrochemical probe includes making the diffusion hole in the probe body after the electrolyte layers have been laminated together and before the layers are sintered.

2 Claims, 2 Drawing Sheets

PLANAR ELECTROCHEMICAL PROBE

CROSS REFERENCE TO RELATED APPLICATIONS

The present application claims the right of priority of application P 43 42 005.2 filed in Germany on Dec. 9, 1993, the disclosure of which is incorporated herein by reference.

BACKGROUND OF THE INVENTION

The invention relates to a planar electrochemical probe to determine gas components in gas mixtures, and in particular to such a probe comprising a probe body constructed of laminated layers of solid electrolyte layers, with at least one gas chamber integrated into the probe body and a diffusion hole guided to the gas chamber.

Such a planar electrochemical probe which operates according to the polarographic measuring principle is disclosed, for example, in German Patent No. 38 11 713, wherein both anode and cathode are exposed to the gas mixture to be measured. The cathode is constituted as an inner pump electrode in a gas chamber that is integrated into the probe body. The gas chamber is coupled to the gas mixture via a diffusion hole. In the method disclosed in German patent 38 11 713, the probe element is made by printing on the solid electrolyte layers, which may comprise ceramic films, by way of silk-screen printing technology, by laminating the layers together and by subsequently sintering the layers. The diffusion hole leading to the gas chamber is punched into the solid electrolyte layers before laminating and sintering. Punched solid electrolyte layers result in a poor laminar composite in the vicinity of the diffusion hole. Since the diffusion hole is located in the region of active, functional layers, a poor laminar composite also implies that the functional reliability of the probe is affected.

Additionally, practice has shown that particles (incineration ashes of oil) from the exhaust gas of internal combustion engines are deposited at the functional layers, which also impairs functional reliability. Furthermore, silk-screen pastes are sometimes printed into the diffusion hole during silk-screen printing, which, in extreme cases, may lead to a solid plug, which, in turn, would render the probe inoperative.

It has already been proposed to extend the diffusion hole through the entire body of the probe. Such a configuration, however, considerably limits the stackability of functional layers. Additionally, this creates problems especially in broadband probes that operate with an air reference. In this latter configuration, the reference air duct in the region of the diffusion hole must be moved further back which means that the electrodes are no longer opposite each other, thereby increasing the probe's internal resistance. In addition, the heater cannot be configured to cover the entire surface and must also be sealed vis-a-vis the exhaust gas. This makes manufacture costly and also results in poor temperature distribution in the probe body.

SUMMARY OF THE INVENTION

It is an object of the invention to provide an improved polarographic probe that overcomes the above noted drawbacks.

The above and other objects are accomplished in accordance with the invention by the provision of a planar electrochemical probe to determine gas components in a gas mixture, comprising: a probe body including a plurality of solid electrolyte layers; and at least one gas measurement chamber integrated into the probe body; wherein the probe body includes a diffusion hole guided from a surface of the probe body to the gas measurement chamber, the diffusion hole having a depth extending beyond the gas chamber at least into a solid electrolyte layer adjoining the gas measurement chamber.

According to another aspect of the invention there is provided a method of manufacturing a planar electrochemical probe, comprising: laminating solid electrolyte layers together to form a probe body with a gas measurement chamber integrated into the probe body; making a diffusion hole in the probe body which is guided to the gas measurement chamber after the laminating step; and thereafter sintering the probe body.

The polarographic probe according to the invention offers the advantage that the diffusion hole creates a dead volume below the gas measurement chamber in which particles contained in the exhaust gas, such as incineration ashes of oil, can be deposited, which would otherwise impair the functional layers. The method of the invention has the advantage that the laminar composite of the probe body is enhanced, especially in the region of the functional layers. Additionally, the stackability of the solid electrolyte layers and thus the manufacture of the planar probe, are simplified.

Various advantageous modifications and improvements are possible within the scope of the invention. For example, it is particularly advantageous to produce the diffusion hole by way of laser drilling. Laser drilling offers the advantage that the depth of the blind hole is adjustable via the laser pulse output independently of the thickness of the laminar composite. In order to limit the depth of the blind hole independently of the laser pulse output it is, on the other hand, advantageous if a reflecting layer is integrated into the laminar composite at the end of the diffusion hole. The reflecting layer may also be applied to a layer by way of printing technology.

BRIEF DESCRIPTION OF THE DRAWINGS

The drawings illustrate three embodiments of the invention which are explained in greater detail in the following description.

DETAILED DESCRIPTION OF THE PREFERRED EMBODIMENTS

Figure 1:
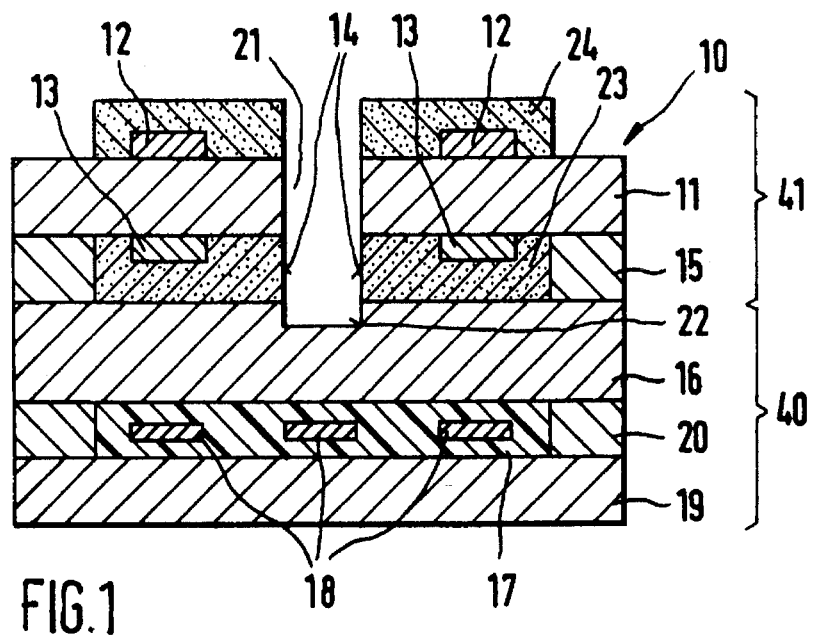
FIG. 1 shows a cross section of the laminar composite of a probe body according to the invention.

Referring to FIG. 1, there is shown an embodiment of the invention which includes a probe body 10 comprised of a pump cell 41, also referred to as a polarographic probe, and a heater unit 40. Pump cell 41 includes a first solid electrolyte layer 11 provided with an outer pump electrode 12 (anode) and an inner pump electrode 13 (cathode). Inner pump electrode 13 is located in a gas chamber 14 which is placed in a second solid electrolyte layer 15. Below solid electrolyte layer 15 is disposed a third solid electrolyte layer 16 which is adjoined by a heating element 18 embedded in an electrically insulating layer 17. Over insulating layer 17 is placed a fourth solid electrolyte layer 19 which is connected to the third solid electrolyte layer 16 via a frame 20. The third and fourth solid electrolyte layers 16, 19 as well as the heating element 18, which is enclosed in the layer 17 and the frame 20, form heater unit 40. The solid electrolyte layers referred to herein are preferably in the form of ceramic films as further described below.

A diffusion hole 21 penetrates first solid electrolyte layer 11, with electrodes 12 and 13, for example, arranged in a ring-shaped manner around the diffusion hole. The diffusion hole 21 leads to gas chamber 14 and extends beyond the latter as a blind hole into third solid electrolyte layer 16. In this manner there is formed below gas chamber 14 a dead volume 22 at the end of diffusion hole 21 in which particles carried in the gas mixture can be deposited, such as incineration ashes of oil. The depth of diffusion hole 21 extends, for example, about 20 to about 200 µm into solid electrolyte layer 16. Diffusion hole 21 and gas chamber 14 form a diffusion duct to inner pump electrode 13, and here it is useful that the gas chamber be filled with a porous material which forms a diffusion barrier 23. Outer pump electrode 12 is also suitably covered with a porous protective layer 24.

Figure 2:
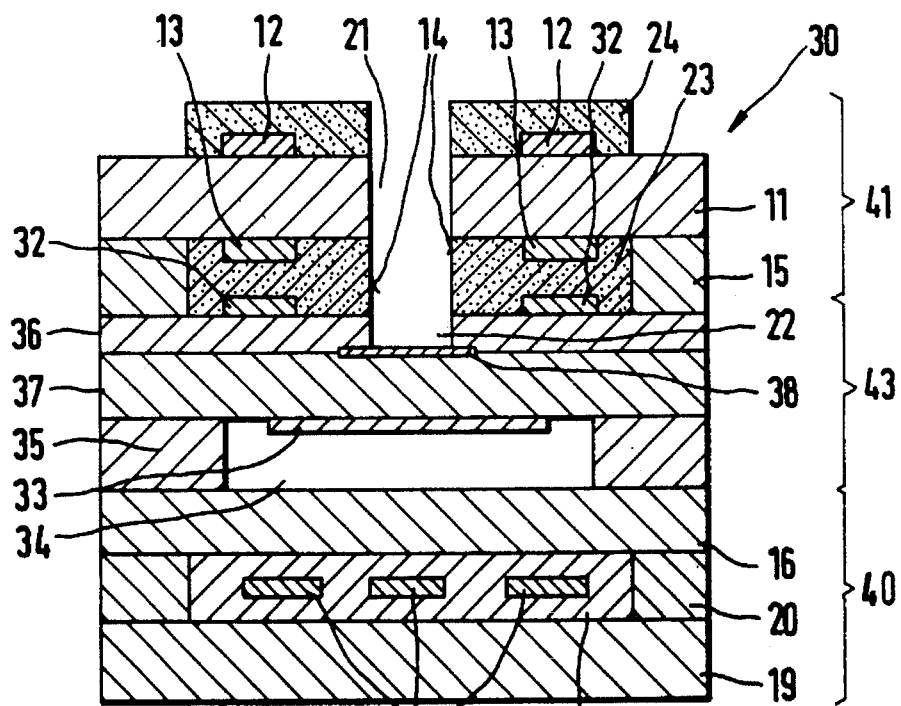
FIG. 2 shows a cross section of a laminar composite of a probe body forming a broadband probe according to another embodiment of the invention.

In contrast to the embodiment shown in FIG. 1, a probe body 30 is shown in FIG. 2 which illustrates a polarographic probe configured as a broadband sensor. The embodiment of FIG. 2 mainly differs from the above-described polarographic probe according to FIG. 1 in that, in addition to pump cell 41, there is provided a concentration cell 43 which functions on the basis of the Nernst principle.

The configuration of pump cell 41 in FIG. 2 essentially corresponds to that in FIG. 1. The concentration cell 43 includes a solid electrolyte layer 36 facing the measurement gas chamber 14 and a solid electrolyte layer 37 facing a reference gas chamber 34. Solid electrolyte layer 36 is provided with a measuring electrode 32 and solid electrolyte layer 37 with a reference electrode 33. Measuring electrode 32 is disposed in gas chamber 14 together with the inner pump electrode 13. It is also possible however, to interconnect inner pump electrode 13 and measuring electrode 32 and position them as an electrode in gas chamber 14. Reference electrode 33 is disposed in reference gas chamber 34 which is incorporated in a further solid electrolyte layer 35 and connected to the atmosphere via a duct that is not shown.

Still referring to FIG. 2, a reflecting layer 38 is disposed at least in the region of diffusion hole 21 between solid electrolyte layer 36 and solid electrolyte layer 37. Like the electrodes, reflecting layer 38 is printed on one of solid electrolyte layers 36, 37 by way of silk-screen printing technology. According to FIG. 2, diffusion hole 21 extends to reflecting layer 38 so that the depth of dead volume 22 is determined by the thickness of the solid electrolyte layer 36. A further solid electrolyte layer 35 adjoins third solid electrolyte layer 16 of heater unit 40 which is constructed according to the first embodiment.

For the manufacture of pump cell 10 according to FIG. 1, outer and inner pump electrodes 12, 13, respectively, and associated conducting tracks are printed on the unsintered solid electrolyte layer 11 made, for example, of yttrium-stabilized $ZrO_2$, by using a customary platinum cermet printing paste. Second solid electrolyte layer 15, also made of yttrium-stabilized $ZrO_2$, contains the gas measurement chamber 14, which, for example, is configured as a circular punch-out. A porous sintering material made, for example, also on an yttrium-stabilized $ZrO_2$ base, having a porosity of, for example, 20 to 30 percent, is placed into the gas measurement chamber 14. Alternatively, a suitably porous formed body be placed in the gas measurement chamber 14 instead of the porous material.

Heater unit 40 is made by printing electrically insulating layer 17 on an $AL_2O_3$ base on the third solid electrolyte layer 16 made of yttrium-stabilized zirconium oxide. Subsequently, the heater element 18 is applied by using a $Pt/Al_2O_3$ cermet paste, a second portion of the electrically insulating layer 17 and the frame 20.

Afterwards, the four solid electrolyte layers 11, 15, 16 19 are laminated together under pressure to form probe body 10. After lamination, probe body 10 is provided with diffusion hole 21, for instance with a laser working unit, inside of the pump electrodes 12, 13, which are arranged in a ring-shaped fashion. Diffusion hole 21 is configured as a blind hole which extends beyond gas measurement chamber 14, into third solid electrolyte layer 16. After diffusion hole 21 is made, probe body 10 is sintered at a temperature of approximately 1400° C. Finally, protective layer 24 is applied at least to outer pump electrode 12 as an engage layer.

Probe body 30 of the broadband probe according to FIG. 2 is made in a similar manner as probe body 10 in FIG. 1 with pump cell 41 being made as described above and with the additional solid electrolyte layers 35, 36, 37 also being laminated together. In contrast to the pump cell 41 according to FIG. 1, in the broadband sensor according to FIG. 2, the reflecting layer 38 consisting of Pt, for example, is applied in an additional silk-screen printing step onto the solid electrolyte layer 36 or the solid electrolyte layer 37 at least in the region where the diffusion hole 21 will later have to be made.

Just like the manufacture of pump cell 41 according to FIG. 1, the diffusion hole 21 is made also after the individual solid electrolyte layers have been laminated together. In the present embodiment according to FIG. 2, the diffusion hole 21 is also made with a laser beam. In this process the depth of the diffusion hole is limited by the reflecting layer 38. The laser is turned off via a special arrangement that recognizes the reflected laser radiation. This embodiment offers the advantage that a precise preselection of the laser pulse output corresponding to the planned working depth is not necessary prior to laser drilling. But in the broadband sensor according to FIG. 2, it is equally possible to determine the depth of the diffusion hole 21 via the laser pulse output. If this is done, it is not necessary to include reflecting layer 38 and, instead of the two solid electrolyte layers 36, 37, a single solid electrolyte layer is used.

In place of the solid electrolyte layers that do not contribute to the function of the pump cell 41 and of the concentration cell 43, other materials may also be used. These layers do not have to offer an oxygen-ion conducting function. A preferred material would be, for example, $Al_2O_3$.

Figure 3:
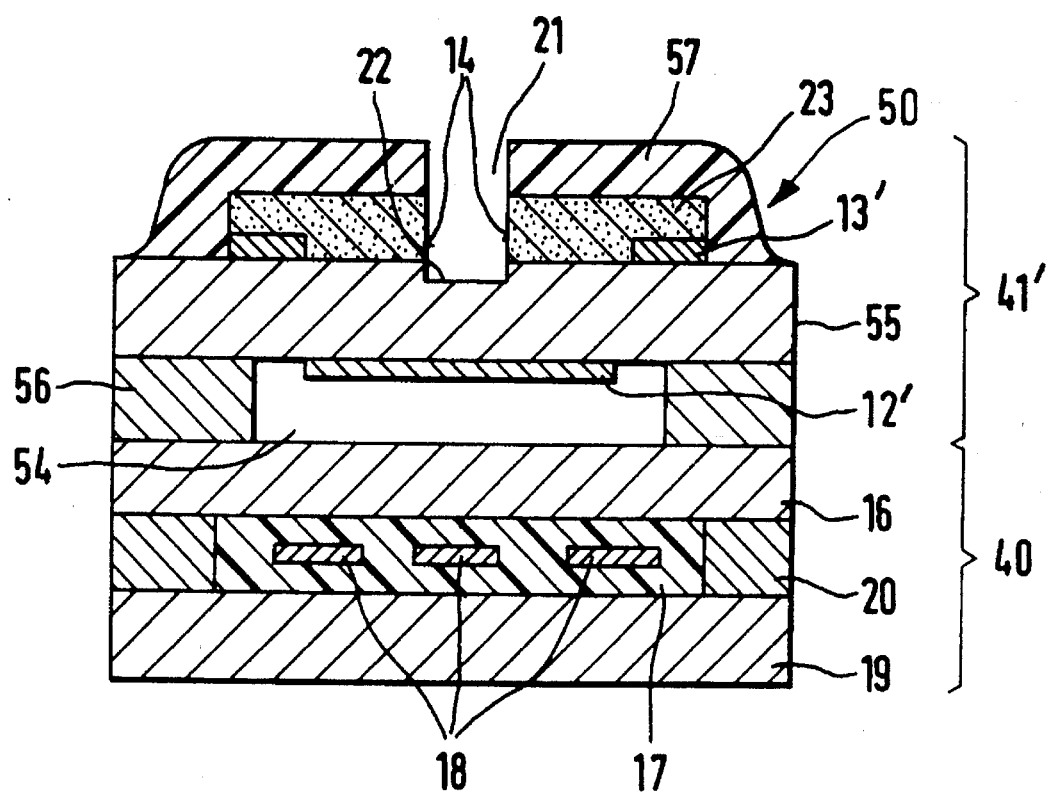
FIG. 3 a cross section through another embodiment of a probe body according to the invention.

FIG. 3 shows a further embodiment of a planar electrochemical probe comprising a probe body 50 which includes a pump cell 41', wherein within a reference gas chamber layer 56 there is provided a reference gas chamber 54 which is connected to the atmosphere by a duct (not shown). In reference gas chamber 54 a pump electrode 12' having the effect of an anode is arranged at a solid electrolyte layer 55. Solid electrolyte layer 55 has the function of the first solid electrolyte layer 11 of the first embodiment according to FIG. 1. Heater unit 40 adjoins the reference gas chamber layer 56, with pump cell 41' and the heater unit 40 being laminated together. Pump electrode 13' is then printed on the solid electrolyte layer 55 acting as a cathode. A diffusion barrier 23 forming the gas measurement chamber 14 is printed on top of pump electrode 13' and a gas-tight resist coating 57 is formed over diffusion barrier 23 and pump electrode 13' such that resist coating 57 extends onto the surface of solid electrolyte layer 55 as shown in FIG. 3. Once the printed layers described above have dried, the diffusion hole 21 is formed by way of laser drilling, with the diffusion hole 21 extending through the printed layers into solid electrolyte layer 55 adjoining the printed layers. Diffusion hole 21 forms a dead volume 22 in solid electrolyte layer 55. After making diffusion hole 21, the probe body 50 is sintered as in the other embodiments.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. A planar electrochemical probe to determine gas components in a gas mixture, comprising:

a probe body including a plurality of solid electrolyte layers;

at least one gas measurement chamber filled with a porous material integrated into the probe body; wherein said probe body includes a blind diffusion hole guided from a surface of said probe body through the porous material of said gas measurement chamber, the diffusion hole having a depth extending beyond said gas measurement chamber at least into a solid electrolyte layer adjoining said gas measurement chamber to create a volume in said adjoining solid electrolyte layer.

2. The probe according to claim 1, wherein the volume in said adjoining solid electrolyte layer has a depth of about 20 to about 200 micrometers.

\* \* \* \* \*